(12) United States Patent
Kim et al.

(10) Patent No.: US 8,449,461 B2
(45) Date of Patent: May 28, 2013

(54) SURGICAL RETRACTOR

(75) Inventors: Young-Woo Kim, Goyangsi (KR);
Kwang-Gi Kim, Goyangsi (KR);
Kyoung-Won Nam, Goyangsi (KR)

(73) Assignee: National Cancer Center (KR)

( * ) Notice: Subject to any disclaimer, the term of this patent is extended or adjusted under 35 U.S.C. 154(b) by 361 days.

(21) Appl. No.: 12/846,558

(22) Filed: Jul. 29, 2010

(65) Prior Publication Data

US 2011/0040152 A1 Feb. 17, 2011

(30) Foreign Application Priority Data

Aug. 13, 2009 (KR) .......................... 10-2009-0074507

(51) Int. Cl.
*A61B 1/32* (2006.01)
(52) U.S. Cl.
USPC ............. 600/210; 600/37; 600/204; 600/215; 600/226; 600/235
(58) Field of Classification Search
USPC .............................. 600/201–249; 606/37, 151
See application file for complete search history.

(56) References Cited

U.S. PATENT DOCUMENTS

| 5,267,554 | A |   | 12/1993 | Wilk |   |
|---|---|---|---|---|---|
| 5,582,577 | A | * | 12/1996 | Lund et al. | 600/204 |
| 2006/0149135 | A1 | * | 7/2006 | Paz | 600/201 |

FOREIGN PATENT DOCUMENTS

| JP | 1996-019546 | 1/1996 |
|---|---|---|
| JP | 2005-524475 | 8/2005 |
| JP | 2008-048907 | 3/2008 |
| KR | 10-1999-0019325 | 3/1999 |
| KR | 10-2003-0085353 | 11/2003 |
| WO | WO-03/094744 | 11/2003 |
| WO | WO 2008/023481 | 2/2008 |
| WO | WO-2008/143133 | 11/2008 |
| WO | WO-2009/032611 | 3/2009 |

OTHER PUBLICATIONS

Yoshihisa Sakaguchi "New technique for the retraction of the liver in laparoscopic gastrectomy", Spring Science+Business Media, LLC 2008, Jan. 24, 2008.

* cited by examiner

*Primary Examiner* — Todd Manahan
*Assistant Examiner* — Jessica Weiss
(74) *Attorney, Agent, or Firm* — Foley & Lardner LLP; Michel Morency

(57) ABSTRACT

Provided is a surgical retractor capable of preventing an organ of a human body from being damaged when the organ of the human body positioned over a surgical area in the human body is lifted up. The surgical retractor includes a support body including a plurality of support members that are inserted below an organ of a human body which is positioned over a surgical area in the body of a patient to lift the organ of the human body in an upward direction, the plurality of support members being fastened to a joint, and a protective film member joined to the support body to cover a region between the support members, and configured to enclose and protect a lower surface of the organ of the human body.

14 Claims, 12 Drawing Sheets

US 8,449,461 B2

SURGICAL RETRACTOR

CLAIM FOR PRIORITY

This application claims priority to Korean Patent Application No. 2009-0074507 filed on Aug. 13, 2009 in the Korean Intellectual Property Office (KIPO), the entire contents of which are hereby incorporated by reference.

BACKGROUND

1. Technical Field

Example embodiments of the present invention relate in general to a surgical instrument, and more specifically, to a surgical retractor for lifting an organ of a body of a patient during minimally invasive surgery (MIS) using laparoscopy instruments.

2. Related Art

In general, when performing laparotomy in order to treat a patient, an incision is large and a bleeding amount occurring at the surgical procedure is high, so that the patient recovers slowly. In addition, such a surgical procedure leaves a large scar, causing problems later in the patient's life. In order to overcome drawbacks of the laparotomy such as these, new surgical methods such as minimally invasive surgery (MIS) using laparoscopy instruments have been developed.

MIS is a surgical method of cutting only a minimum portion on a surface of a body of a patient using an elongated instrument specifically designed to minimize the incision necessary for the surgery. Because of the advantages of MIS, such as that the incision necessary for the surgical procedure is small, the bleeding amount is significantly less than that of the laparotomy, a postsurgical recovery period of the patient is short, and the outwardly visible scar is small. The number of surgical procedures using MIS is dramatically increasing.

A surgical retractor is used to increase a field of vision of a surgical area and expand a working region of various surgical instruments by lifting organs of the human body which are positioned over the surgical area during MIS using laparoscopy instruments. For example, a liver retractor is used to lift a portion of a liver in an upward direction covering a stomach so that the stomach to be operated on can be seen clearly by an endoscope when operating on the stomach using laparoscopy instruments.

However, existing surgical retractors including the liver retractor have a drawback in that installation is complicated. For example, a separate large fixing platform may need to be installed at an outer position.

Meanwhile, a Y-shaped liver retractor is disclosed in "New technique for the retraction of the liver in laparoscopic gastrectomy" (Yoshihisa Sakaguchi, 2008) in Surg Endosc 22:2532-2534. The liver retractor includes a Y-shaped support member configured to support a lower portion of a liver and a lift wire fixed to each of three end portions of the support member, and lifts a portion of the liver covering an upper portion of the stomach during a surgical procedure.

However, the liver retractor has a problem in that the lifted lower surface of the liver may incur mild to severe damage during the operation, since there is no function of protecting a lower surface of the liver positioned in a region between the Y-shaped support members.

SUMMARY

Accordingly, example embodiments of the present invention are provided to substantially obviate one or more problems due to limitations and disadvantages of the related art.

Example embodiments of the present invention provide a surgical retractor capable of preventing an organ of a human body from being damaged when the organ of the human body positioned over a surgical area in the human body is lifted up.

Example embodiments of the present invention also provide a surgical retractor which can be easily installed without installing a separate large fixing platform at an outer position.

Additional aspects of the invention will be set forth in the description which follows, and in part will be apparent from the description, or may be learned by practice of the invention.

In some example embodiments, a surgical retractor includes a support body including a plurality of support members that are inserted below an organ of a human body which is positioned over a surgical area in the body of a patient to lift the organ of the human body in an upward direction, the plurality of support members being fastened to a joint; and a protective film member joined to the support body to cover a region between the support members, and configured to enclose and protect a lower surface of the organ of the human body.

The support member may include a first support member having an end portion positioned on the joint; and second and third support members fastened to the joint at one ends thereof to rotate around the joint in a leftward direction and a rightward direction, respectively, with respect to the first support member. The support member may further include a fourth support member fastened to the joint at one end thereof to rotate around the joint in an upward direction and a downward direction with respect to the first support member.

The support members may be formed in a shape of a circular rod or plate-shaped elongated bar, and the joint may have a hinge-type structure or a ring-type structure.

The protective film member may be made of a flexible material such as fabric or polymer to be folded or unfolded in cooperation with rotation of the support members around the joint.

The protective film member may be attached to the first, second and third support members to cover a region between the first support member and the second support member, and a region between the first support member and the third support member.

The surgical retractor may further include a fixing fixture fastened to the support body to lift and fix the organ of the human body in an upward direction.

End portions of the support members may be provided with fixing hooks each fixed to the fastening fixture.

The fastening fixture may include a fixing body configured to penetrate a skin of the human body adjacent to a surgical area of the patient, and provided with a wire hole; and a bridge member inserted into the body of the patient through the wire hole, and locked to each of the fixing hooks of the support members to lift the support body in an upward direction.

In addition, the fixing body may include a fixing plate seated on the skin of the human body adjacent to the surgical area, and having the wire hole formed in its center portion; and a guide tube extending from a lower portion of the fixing plate to communicate with the wire hole, and configured to penetrate the skin of the body of the patient to guide the bridge member inserted through the wire hole.

Moreover, the bridge member may include a locking wire locked to each of the fixing hooks of the support members; a guide wire engaged with the locking wire to insert the locking wire into the wire hole; and a handle engaged with the guide wire.

The locking wire may be formed in a shape of a closed-loop ring, and the guide wire may be made of a flexible material.

The fixing plate may have a wire fixing member for fixing the guide wire.

The wire fixing member may include a first fixing member provided on one side of an upper surface of the fixing plate, and having a primary fixing groove to which the guide wire is inserted and primarily locked; and a second fixing member provided on the other side of the upper surface of the fixing plate, and having a secondary fixing groove formed in a widthwise direction with respect to the first fixing groove such that the guide wire primarily locked and fixed by the first fixing member is inserted and secondarily locked.

A bending member may be interposed between the first fixing member and the second fixing member to bend the guide wire in a curve.

In other example embodiments, a surgical retractor includes a body inserted below an organ of a human body which is positioned over a surgical area in the body of a patient to lift the organ of the human body in an upward direction; and a fastening fixture inserted into the body of the patient to lift and fix the body in an upward direction using a fastening wire locked to the body.

The body may include a plurality of support members fastened to a joint; a protective film member engaged with the support member to cover a region between the support members; and a fixing hook formed at end portions of the support members and fixed to the fastening wire.

BRIEF DESCRIPTION OF DRAWINGS

Example embodiments of the present invention will become more apparent by describing in detail example embodiments of the present invention with reference to the accompanying drawings, in which.

DETAILED DESCRIPTION OF EXAMPLE EMBODIMENTS

Figure 1:
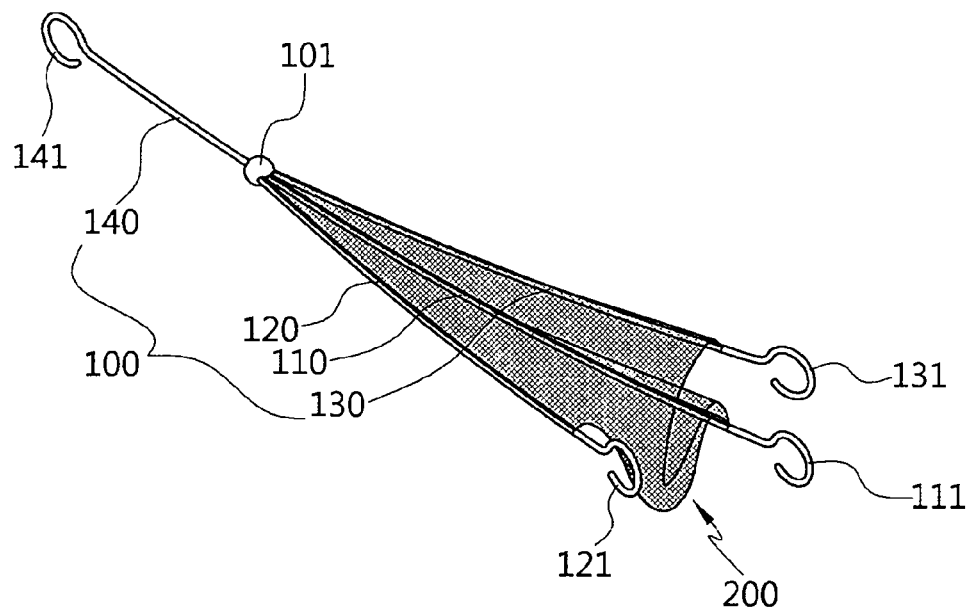
FIGS. 1 and 2 are perspective views schematically illustrating a surgical retractor according to an example embodiment of the present invention.

Example embodiments of the present invention are disclosed herein. However, specific structural and functional details disclosed herein are merely representative for purposes of describing example embodiments of the present invention, however, example embodiments of the present invention may be embodied in many alternate forms and should not be construed as limited to example embodiments of the present invention set forth herein.

Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention. Like numbers refer to like elements throughout the description of the figures.

It will be understood that, although the terms "first," "second," etc. may be used herein to describe various elements, these elements should not be limited by these terms. These terms are only used to distinguish one element from another. For example, a first element could be termed a second element, and, similarly, a second element could be termed a first element, without departing from the scope of the present invention. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (i.e., "between" versus "directly between," "adjacent" versus "directly adjacent," etc.).

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Although a surgical retractor for lifting an organ, in particular, a liver, of a body of a patient during minimally invasive surgery (MIS) using laparoscopy instruments will be described hereinafter, the present invention is not limited thereto. It would be understood from those skilled in the art that it can be used as a surgical retractor capable of lifting other organs of the human body, such as a stomach or kidney.

Figure 2:
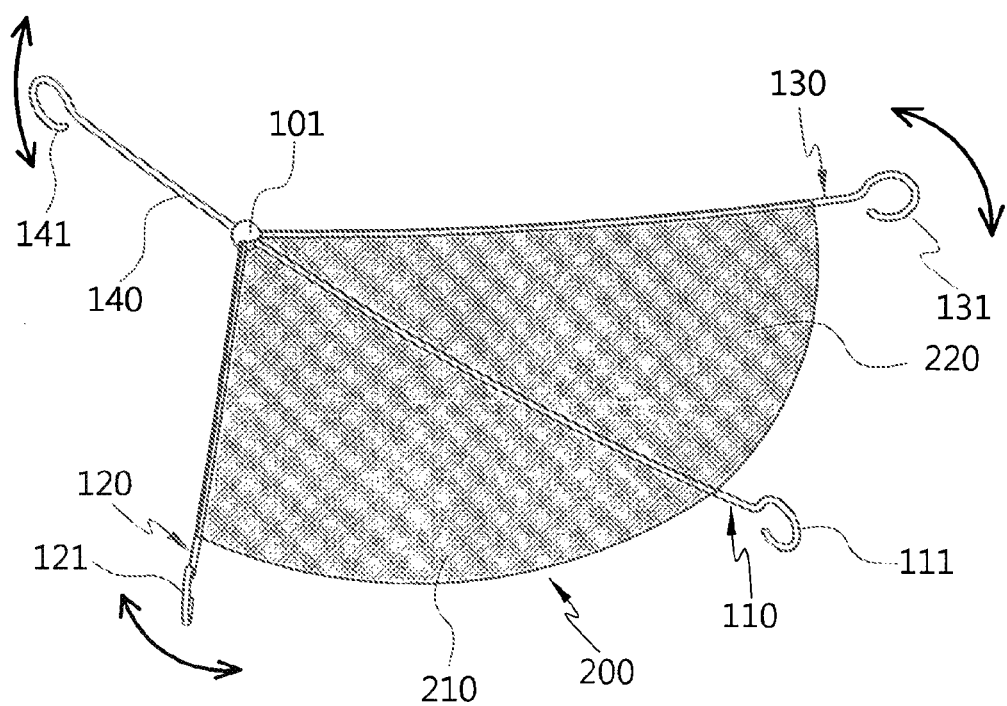

FIGS. 1 and 2 are perspective views schematically illustrating a surgical retractor according to an example embodiment of the present invention, in which FIG. 1 is a view illustrating a folded state of the surgical retractor, and FIG. 2 is a view illustrating an unfolded state of the surgical retractor.

As shown in FIGS. 1 and 2, a surgical retractor according to an example embodiment of the present invention may include a support body 100 and a protective film member 200.

The support body 100 includes a plurality of support members that are inserted below an organ of a human body which is positioned over a surgical area in the body of a patient, for example, a liver 1 (refer to FIG. 11) which is the organ of the human body covering an upper portion of a stomach, to lift a portion of the liver in an upward direction when operating on the stomach. Here, the support members are fastened to a joint 101.

The protective film member 200 is joined to the support body 100 to cover regions between support members 110, 120 and 130 which will be described hereinafter, and encloses and protects a lower surface of the liver 1. The protective film member 200 is preferably made of a flexible material, for example, fabric or polymer, which can be folded or unfolded in cooperation with the rotating support members 110, 120, 130 and 140 when the support members 110, 120, 130 and 140 rotate around the joint 101.

In addition, the protective film member 200 may be attached to the first, second and third support members 110, 120 and 130 to cover a region 210 between the first support member 110 and the second support member 120, and a region 220 between the first support member 110 and the third support member 130. Accordingly, the protective film member 200 can be folded or unfolded in the shape of a fan when the second support member 120 and the third support member 130 rotate around the joint 101 in a leftward direction and a rightward direction, respectively, with respect to the first support member 110.

Figure 3:
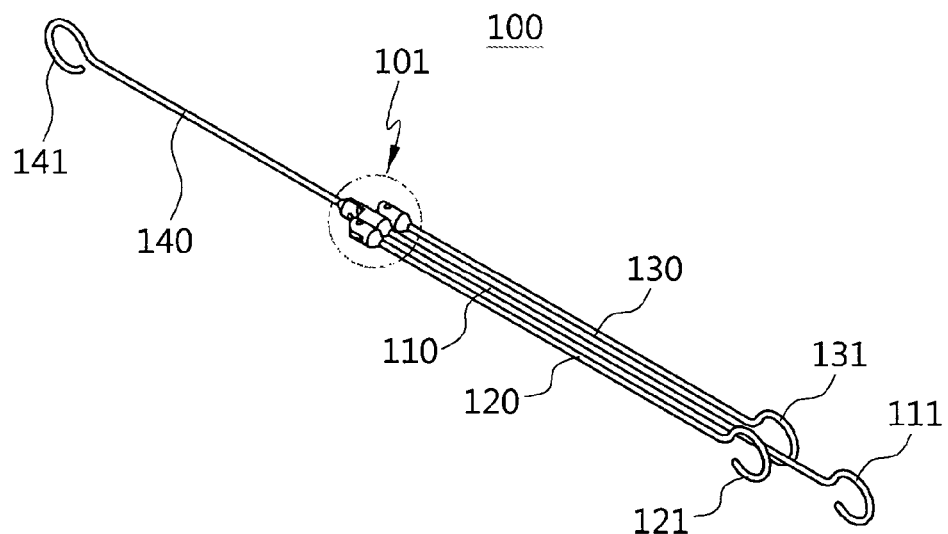
FIGS. 3 and 4 are perspective views illustrating folding and unfolding states of a support body according to an example embodiment of the present invention.
Figure 4:
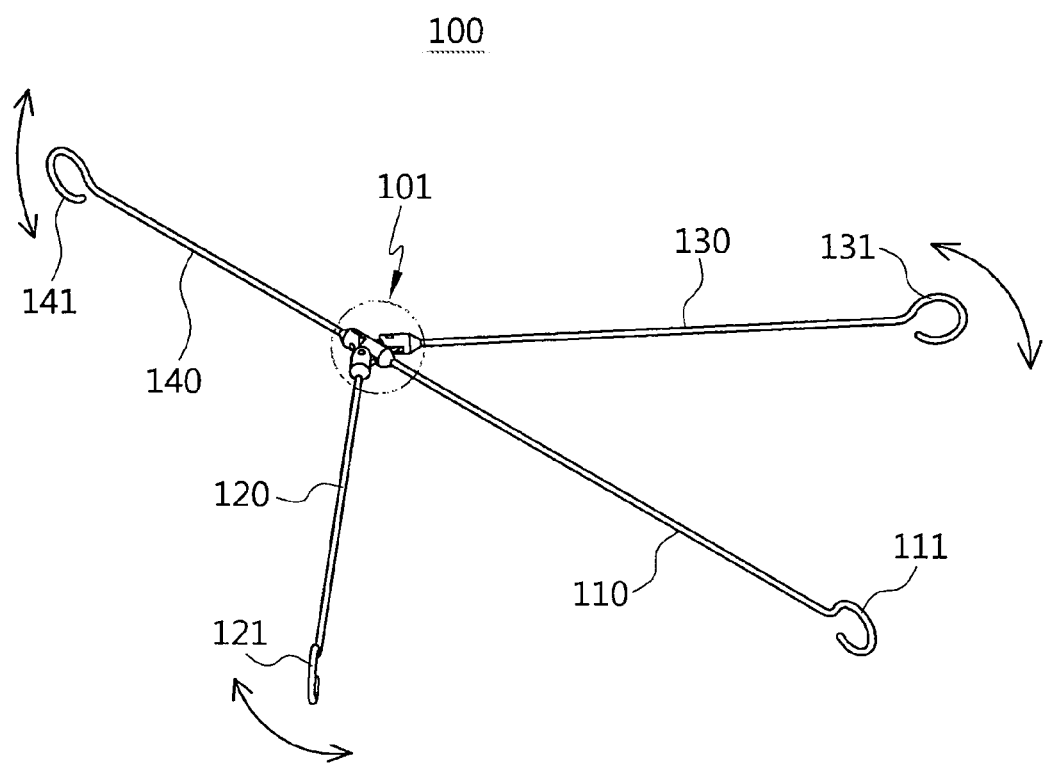

FIGS. 3 and 4 are perspective views illustrating folding and unfolding states of the support body according to an example embodiment of the present invention.

As shown in FIGS. 3 and 4, the support body 100 may include four support members fastened to the joint 101. For example, the support member 100 may include a first support member 110 with an end portion positioned on the joint 101, second and third support members 120 and 130 which are fastened to the joint 101 at one ends thereof such that the second and third support members 120 and 130 rotate around the joint 101 in a leftward direction and a rightward direction, respectively, with respect to the first support member 110, and a fourth support member 140 which is fastened to the joint 101 at one end thereof such that the fourth support member 140 rotates around the joint 101 in an upward direction and a downward direction with respect to the first support member 110. The support members 110, 120, 130 and 140 are preferably made of a metal, plastic, fabric or polymer material which is suitable to a human body and can be elastically transformed to elastically support the liver 1.

Figure 5:
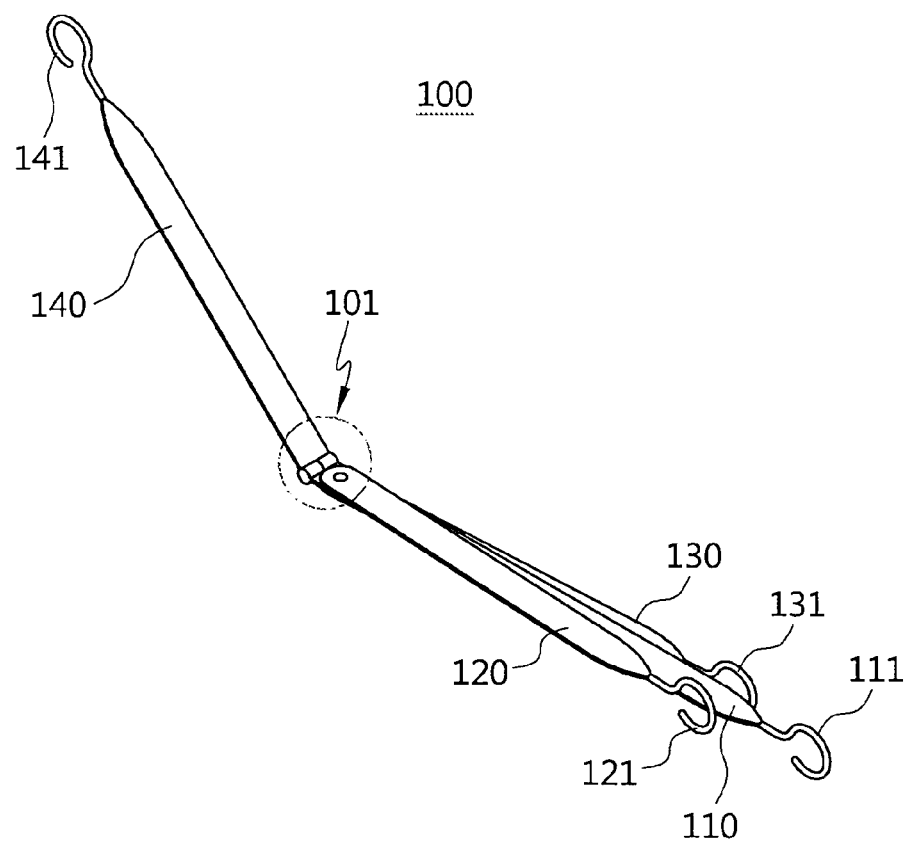
FIGS. 5 and 6 are perspective views illustrating folding and unfolding states of a support body according to another example embodiment of the present invention.
Figure 6:
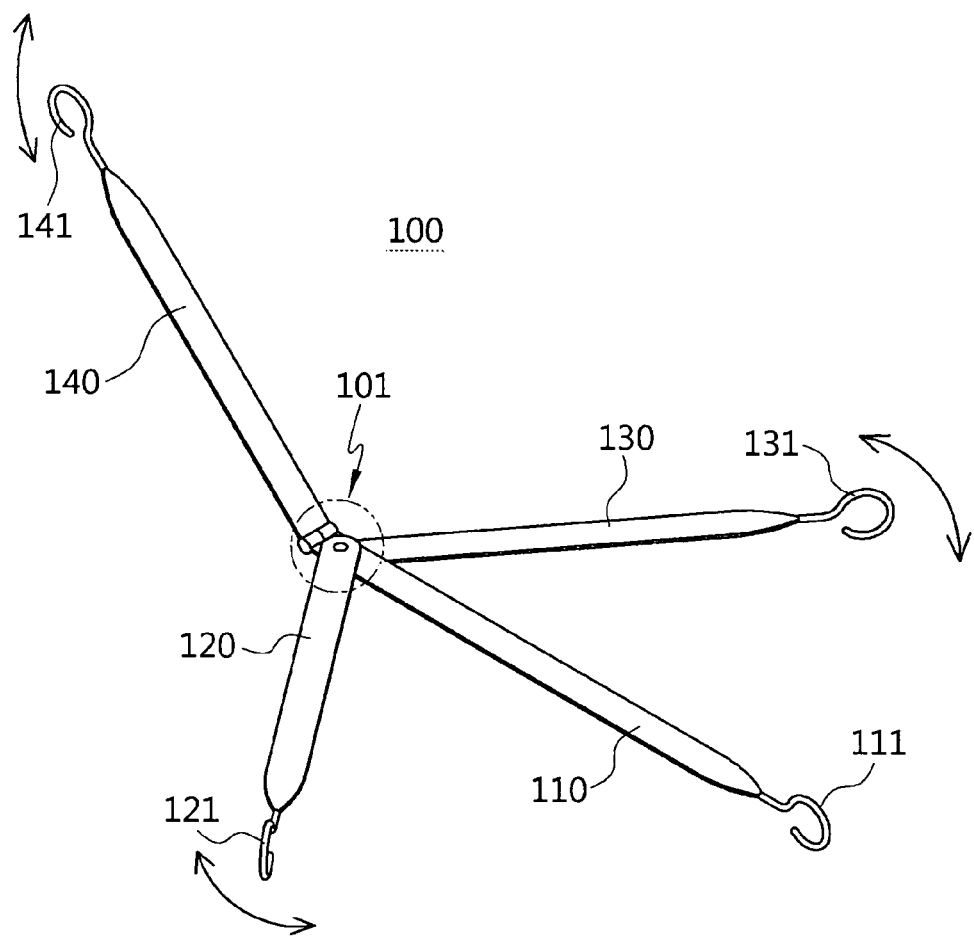
Figure 7:
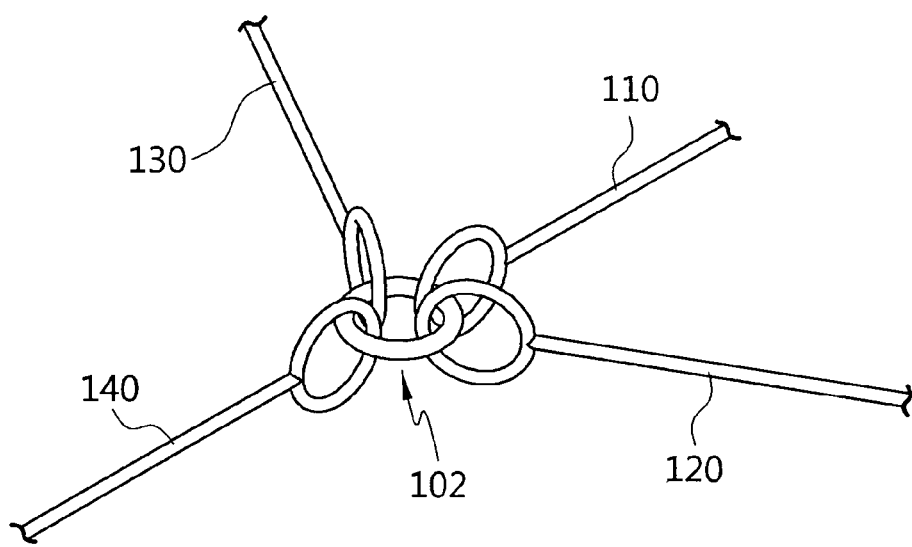
FIG. 7 is a view illustrating a plurality of support members constituting a support body which are fastened to a ring-shaped joint.

Although the support body 100 including four support members 110, 120, 130 and 140 is described and shown in this example embodiment, the present invention is not limited thereto. As long as the support body 100 includes at least three support members, it can obtain a sufficient effect. In addition, although each of the support members 110, 120, 130 and 140 is described and shown in the shape of an elongated circular rod, the present invention is not limited thereto. As shown in FIGS. 5 and 6, each of the support members 110, 120, 130 and 140 may be formed in the shape of a plate-shaped elongated bar. Moreover, although the joint 101 forming a rotational center of the support members 110, 120, 130 and 140 is described and shown to have a hinge-type structure, the present invention is not limited thereto. As shown in FIG. 7, a ring-type joint 102 may be provided.

In addition, the end portions of the support members 110, 120, 130 and 140 are provided with fixing hooks 111, 121, 131 and 141 which are fixed to a fastening wire 321 of a fastening fixture 300 to be described below. In this instance, it is preferable that the lower portions of the fixing hooks 111, 121, 131 and 141 are formed in the shape of a circular ring with its lower portion opened so that the fastening wire 321 is inserted from the lower portion of the fixing hooks 111, 121, 131 and 141 and then is hooked thereto at the upper portion.

Figure 8:
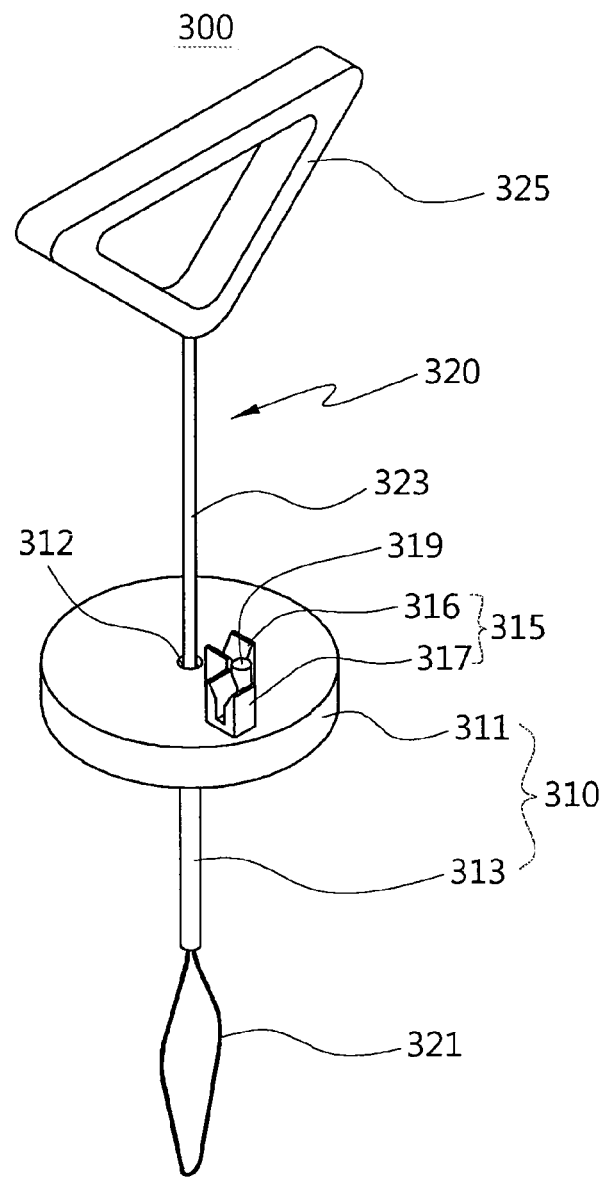
FIG. 8 is a perspective view illustrating a fastening fixture of a surgical retractor according to an example embodiment of the present invention.
Figure 9:
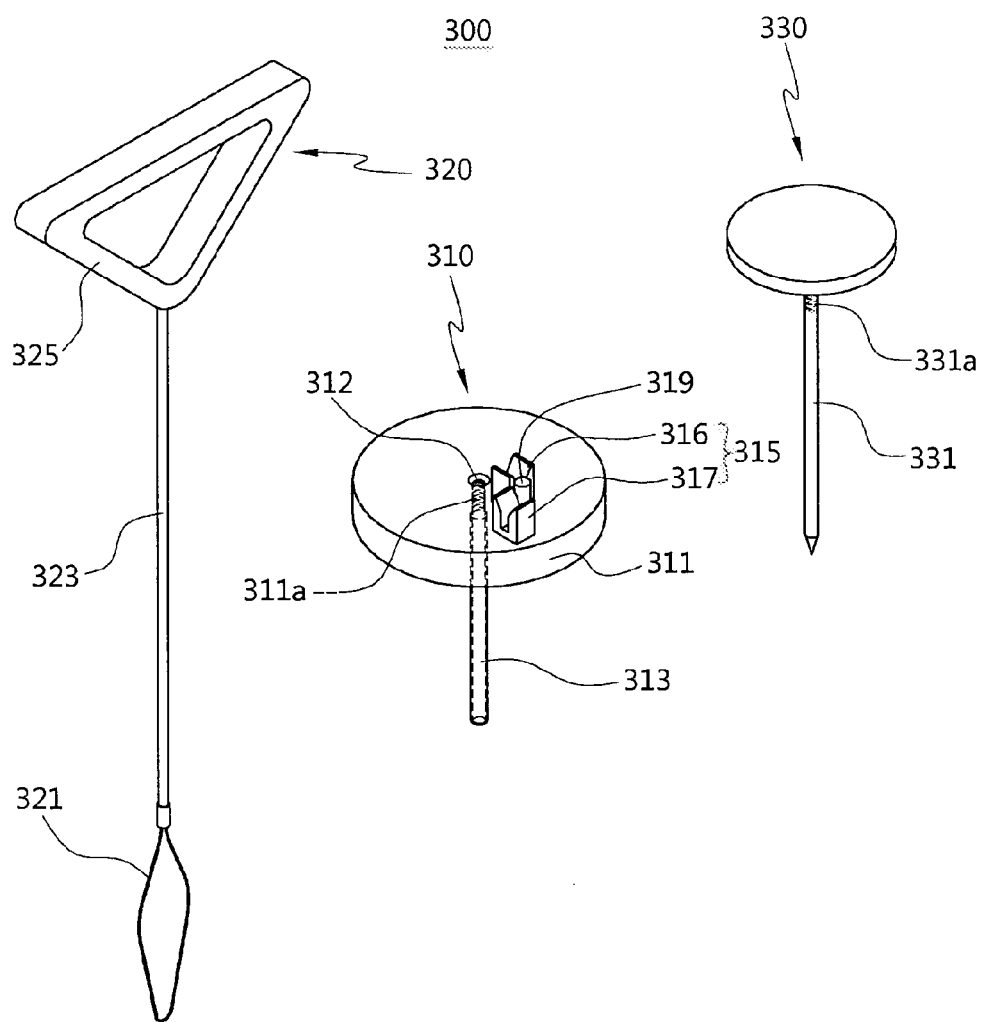
FIG. 9 is an exploded perspective view of the fastening fixture in FIG. 8.

FIGS. 8 and 9 are perspective views illustrating an assembled state and a disassembled state of the fastening fixture of a surgical retractor according to an example embodiment of the present invention.

As shown in FIGS. 8 and 9, a surgical retractor according to the example embodiment of the present invention may further include a fastening fixture 300 fastened to the support body 100 to lift the liver 1 in an upward direction.

The fastening fixture 300 may be constituted of a fixing body 310, a bridge member 320, and a piercing member 330.

The fixing body 310 is installed to penetrate a skin 3 (refer to FIG. 11) of the human body adjacent to the surgical area of the patient.

The fixing body 310 includes a fixing plate 311 seated on the skin 3 of the human body adjacent to the surgical area and provided in its center portion with a wire hole, through which the fastening wire 321 to be described below is inserted into the human body, and a guide tube 313 extended from the lower portion of the fixing plate 311 to communicate with the wire hole 312. The guide tube 313 penetrates the skin 3 of the human body 3 of the patient to guide the fastening wire 321 inserted through the wire hole 312 to the human body. In this example embodiment, although the fixing plate 311 formed in the shape of a circular plate is described and shown, the present invention is not limited thereto. The fixing plate 311 may be formed in the shape of a polygonal plate such as a triangular or rectangular plate.

In addition, the fixing plate 311 may be provided with a wire fixing member 315 for fixing the guide wire 323 of the bridge member 320 to be described below.

The wire fixing member 315 may include a first fixing member 316 provided on one side of the upper surface of the fixing plate 311 and provided with a primary fixing groove 316*a* (refer to FIG. 14) such that the guide wire 323 is forcibly inserted and primarily locked, and a second fixing member 317 provided on the other side of the upper surface of the fixing plate 311 and provided with a secondary fixing groove 317*a* such that the guide wire 323 primarily locked and fixed by the primary fixing member 316 is forcibly inserted and secondarily locked. The secondary fixing groove 317*a* is formed in a widthwise direction, preferably a perpendicular direction, with respect to the first fixing groove 316*a*. The first and second fixing grooves 316*a* and 317*a* may open the upper surface of the first and second fixing members 316 and 317 in a V shape, and a recessed groove having an outer diameter substantially identical to that of the guide wire 323 is extended to the lower portion of the opened surface.

In addition, a bending member 319 for bending the guide wire 323 in a curve may be interposed between the first fixing member 316 and the second fixing member 317 to prevent the guide wire 323 from being damaged. The bending member 319 may be engaged with the upper surface of the fixing plate 311 in a cylindrical shape at a wire bending portion between the first fixing member 316 and the second fixing member 317.

The bridge member 320 is inserted into the body of the patient through the wire hole 312 of the fixing body 310, so that the bridge member 320 is locked to each of the fixing hooks 111, 121, 131 and 141 of the support members 110, 120, 130 and 140 to lift the support body 100 in an upward direction.

The bridge member 320 may include a locking wire 321 locked to each of the fixing hooks 111, 121, 131 and 141 of the support members 110, 120, 130 and 140, a guide wire 323 with a lower end portion engaged with the locking wire 321 to insert the locking wire 321 into the wire hole 312, and a handle 325 engaged with an upper end portion of the guide wire 323. The locking wire 321 is formed in the shape of a closed-loop ring, and is preferably made of a metal material with resilience to have a predetermined curvature such that the locking wire is contracted to easily pass through the inner diameter of the guide tube 313 when the locking wire 321 is inserted into the body of the patient through the wire hole 312 and is expanded in the shape of the closed-loop ring in the body of the patient. In addition, the guide wire 323 may be made of a flexible metal material with a predetermined strength such that the guide wire 323 can support the locking wire 321 in a downward direction and a portion of the guide wire which is exposed from the upper portion of the fixing plate 311 is bent and fixed to the wire fixing member 315. In addition, although the handle 325 is described and shown in the shape of an inverted triangle in this example embodiment, the present invention is not limited thereto. The handle 325 may be formed in various shapes such as a circular or polygonal shape.

The piercing member 330 has a tip which is inserted through the wire hole 312 of the fixing body 310 to pierce the skin of the human body, so that the fixing body 310 penetrates the skin 3 of the human body and then is inserted. The piercing member 330 is formed in the shape of a general tack, but is not limited thereto. The piercing member 330 may be formed in various shapes.

In addition, a needle 331 of the piercing member 330 may be provided with a male threaded portion 331a at an upper outer diameter portion thereof, and an inner diameter portion of the wire hole 312 may be provided with a female threaded portion 311a, so that a clearance is not generated in upper and lower directions at the piercing member 330 inserted into the wire hole 312 of the fixing body 310. Although the fixing body 310 and the piercing member 330 are configured to be threadedly engaged with each other in this example embodiment, the present invention is not limited thereto. Any one of the fixing body 310 and the piercing member 330 may be provided with a locking boss (not illustrated), and the other may be provided with a locking groove (not illustrated), so that the fixing body 310 and the piercing member 330 can be locked to each other.

The surgical retractor according to the present invention may include a body which is inserted below the liver 1 covering the upper portion of the stomach, to lift the liver in an upward direction when operating on the stomach, and a fastening fixture 300 for lifting the body in an upward direction using the fastening wire 321 which is inserted into the body of the patient and is locked to the body. In addition, the body may include a plurality of support members 110, 120, 130 and 140 that are fastened to the joint 101, a protective film member 200 for covering regions between the support members 110, 120 and 130, and fixing hooks 111, 121, 131 and 141 formed at the end portions of the support members 110, 120, 130 and 140 and fastened to the fastening wire 321. The support members 110, 120, 130 and 140, the protective film member 200, the fixing hooks 111, 121, 131 and 141, and the fastening fixture 300 which constitute the surgical retractor according to the example embodiment of the present invention are substantially identical to those described and shown in FIGS. 1 to 9, and thus the description thereof will be omitted.

The surgical retractor according to the example embodiment of the present invention can be used to increase a field of vision for a surgical area and expand a working region of various surgical instruments by lifting the liver 1 covering the upper portion of the stomach when operating on the stomach.

More specifically, the surgical retractor constituted of the support body 100 and the protective film member 200 is inserted into the body of the patient through a trocar (not illustrated). In this instance, a separate instrument (not illustrated) for insertion of the surgical retractor is used, and after the support body 100 is connected to the end portion of the insertion instrument, the surgical retractor is transferred to a desired position in the body of the patient. For example, in order to support the liver 1 by lifting a portion of the liver 1 covering the upper portion of the stomach when operating on the stomach, the surgical retractor constituted of the support body 100 and the protective film member 200 is moved to a position below the liver using the insertion instrument.

Figure 10:
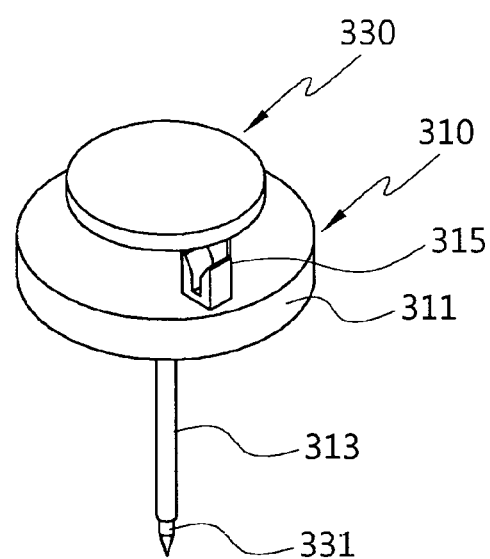
FIGS. 10 to 14 are views illustrating a process of lifting and fixing an organ of a human body using a surgical retractor according to an example embodiment of the present invention.

Next, as shown in FIG. 10, the piercing member 330 is inserted into and fastened to the wire hole 312 formed in the fixing body 310 of the fastening fixture 300. In this instance, the tip of the piercing member 330 protrudes from the lower end portion of the guide tube 313 of the fixing plate 311, and then is exposed.

Figure 11:
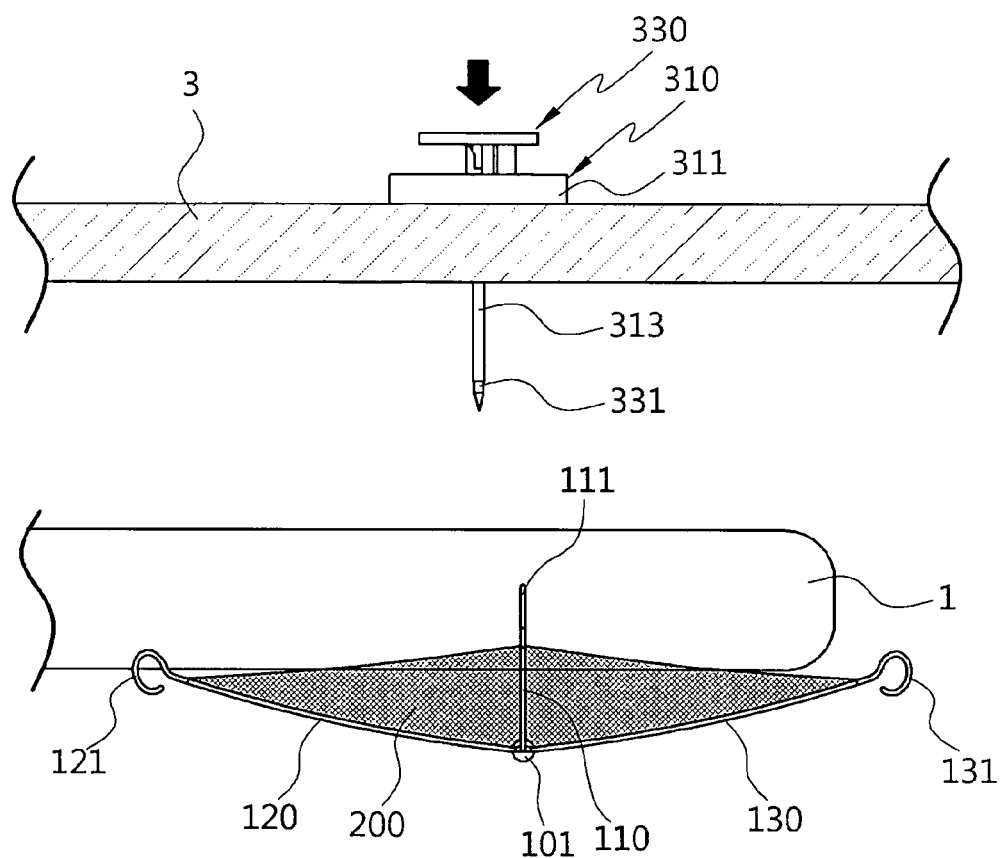

As shown in FIG. 11, after the fixing body 310 is installed to penetrate the skin 3 of the human body by piercing the skin 3 of the human body positioned over the liver 1 using the piercing member 330 which is connected to the fixing body 310, the piercing member 330 is separated and removed from the fixing body 310.

Figure 12:
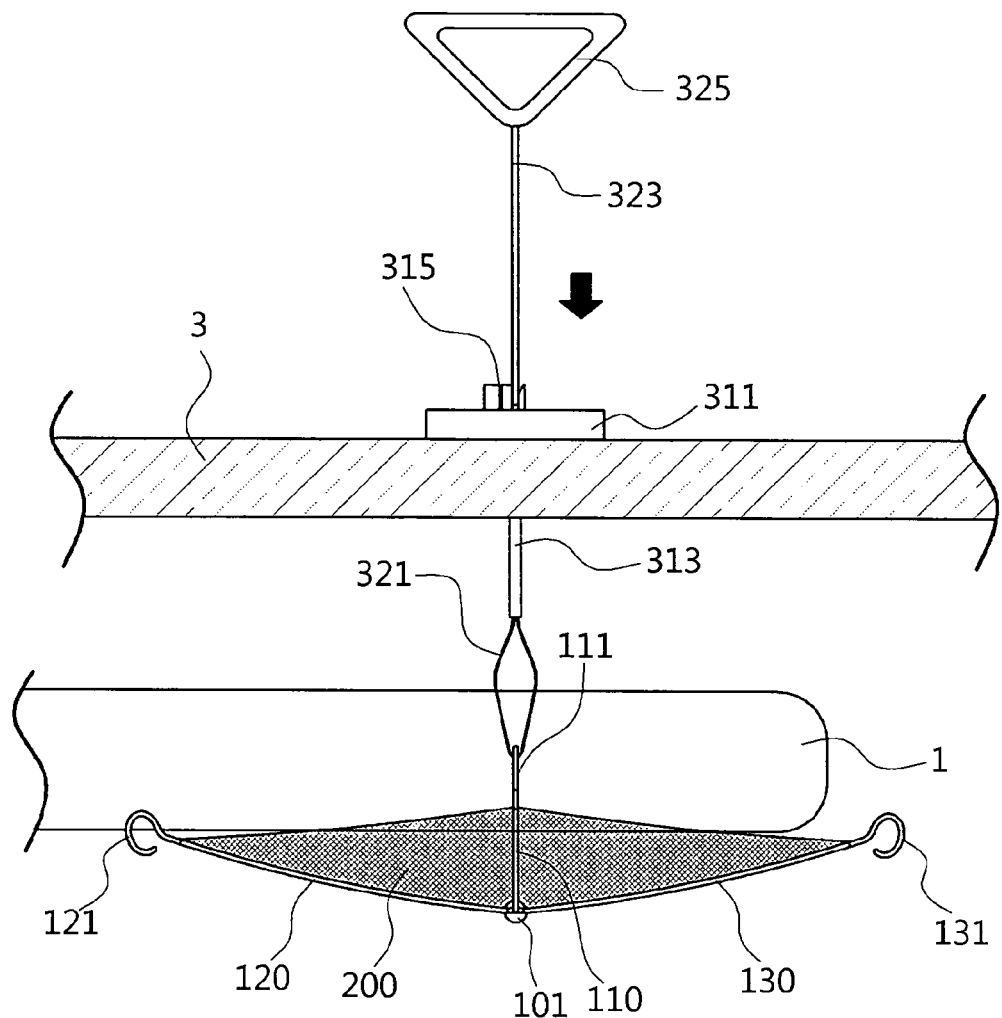

Next, as shown in FIG. 12, after the bridge member 320 is inserted into the wire hole 312 of the fixing body 310 and is led to the human body, the fastening wire 321 of the bridge member 320 is locked to the fixing hook 111 of the first support member 110.

Figure 13:
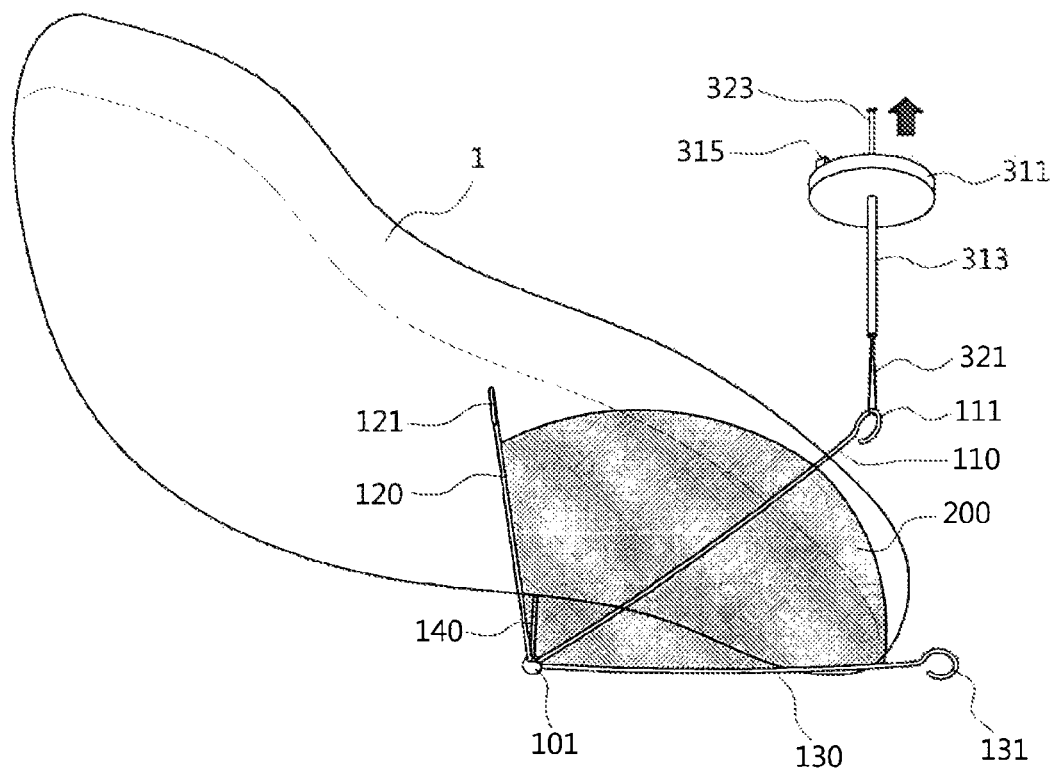

As shown in FIG. 13, if the bridge member 320 is pulled up, the first support member 110 locked to the fastening wire 321 lifts one side of the liver 1 in an upward direction. After the second support member 120 and the third support member 130 are respectively rotated around the joint 101 and unfolded in the leftward direction and the rightward direction with respect to the first support member 110, the second to fourth support members 120, 130 and 140 are locked to the fastening fixture 300 to lift the other side of the liver 1 in the upward direction using the same method as the method of fastening the first support member 110. In this instance, the support members 110, 120, 130 and 140 may be made of a metal, plastic, fabric or polymer material which is suitable to a human body and can be elastically transformed to elastically support the liver 1. The protective film member 200 made of a flexible material, for example, fabric or polymer, is unfolded to the lower surface of the liver 1 to cover the region between the support members in a state in which the support members 110, 120, 130 and 140 lift the liver 1 in an upward direction, thereby preventing the surface of the liver 1 from being damaged.

Although the support members 110, 120, 130 and 140 are fastened in the order thereof in this example embodiment, the fastening order of the support members 110, 120, 130 and 140 is not limited thereto. The fastening order may be determined by optional selection of a surgeon.

Figure 14:
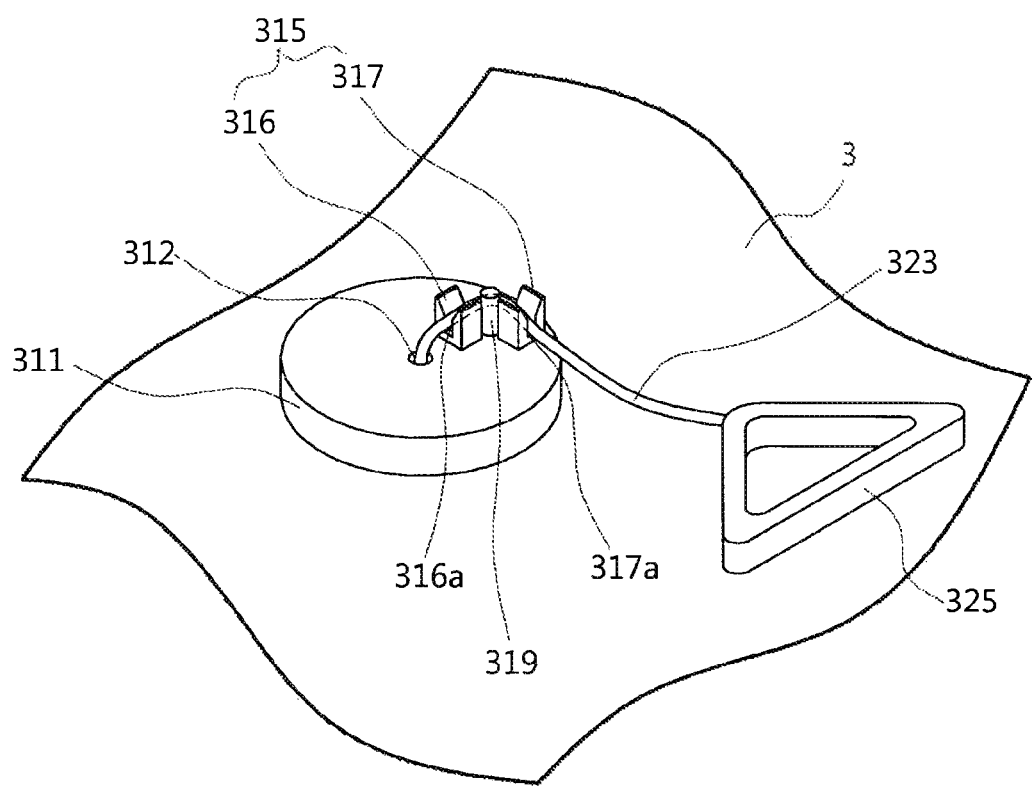

Finally, as shown in FIG. 14, the fastening is completed by fixing the guide wire 323 connected to the fastening wire 321 to the fixing body 310 so that the surgical retractor constituted of the support body 100 and the protective film member 200, which is inserted into the human body and is locked to the fastening wire 321, maintains the lifted state of the liver 1. For example, after the guide wire 323 is forcibly inserted into the first fixing groove 316a of the first fixing member 316 and primarily locked thereto, the guide wire 323 may be forcibly inserted into the secondary fixing groove 317a of the second fixing member 317 which is formed in a perpendicular direction to the primary fixing groove 316a and then secondarily locked thereto. In this instance, a cylindrical bending member 319 for bending the guide wire 323 in a curve may be interposed between the first fixing member 316 and the second fixing member 317 to prevent the guide wire 323 from being damaged.

With a surgical retractor including a liver retractor according to the present invention, since there is no necessary to install a separate large fixing platform at an outer portion, the installation working is very simple.

In addition, since support members are preferably made of a metal, plastic, fabric or polymer material which can be elastically transformed to elastically support the liver, it is possible to minimize the damage of the liver during the operation.

Moreover, since a flexible protective film member is unfolded to cover the region between the support members in a state in which the support members lift the liver in an upward direction, thereby enclosing and protecting the lower surface of the liver and thus preventing the surface of the liver from being damaged.

Also, the fastening can be easily performed by locking a fastening wire of a fastening fixture to fastening hooks formed at end portions of the support members.

In addition, since the fastening fixture with a small diameter is used, there is an advantage in that little scar is left on the surface of the human body after the operation.

While the example embodiments of the present invention and their advantages have been described in detail, it should be understood that various changes, substitutions and alterations may be made herein without departing from the scope of the invention.

What is claimed is:

1. A surgical retractor comprising: a support body including a plurality of support members that are adapted to be inserted below an organ of a human body which is positioned over a surgical area in the body of a patient to lift the organ of the human body in an upward direction, the plurality of support members being fastened to a joint, wherein end portions of the support members are provided with fixing hooks; a protective film member joined to the support body to cover a region between the support members, and configured to enclose and protect a lower surface of the organ of the human body; and a fastening fixture configured to be fastened to the support body to lift and fix the organ of the human body in an upward direction, wherein the fastening fixture includes a fixing body configured to penetrate the skin of the human body adjacent to the surgical area of the patient, the fixing body including a fixing plate adapted to be seated on the skin of the human body adjacent to the surgical area and having a wire hole formed in its center portion; and a bridge member adapted to be inserted into the body of the patient through the wire hole, and locked to one of the fixing hooks of the support members to lift the support body in an upward direction wherein the support body includes: a first support member having an end portion positioned on the joint; and second and third support members fastened to the joint at one end of each to rotate around the joint in a leftward direction and a rightward direction, respectively, with respect to the first support member.

2. The surgical retractor of claim 1, wherein the support body further includes a fourth support member fastened to the joint at one end thereof to rotate around the joint in an upward direction and a downward direction with respect to the first support member.

3. The surgical retractor of claim 2, wherein the protective film member is attached to the first, second and third support members to cover a region between the first support member and the second support member, and a region between the first support member and the third support member.

4. The surgical retractor of claim 1, wherein the support members are formed in a shape of a circular rod or plate-shaped elongated bar.

5. The surgical retractor of claim 1, wherein the joint has a hinge-type structure or a ring-type structure.

6. The surgical retractor of claim 1, wherein the protective film member is made of a flexible material to be folded or unfolded in cooperation with rotation of the support members around the joint.

7. The surgical retractor of claim 1, wherein the fastening fixture further includes a piercing member which is inserted through the wire hole of the fixing body to pierce the skin of the human body, so that the fixing body penetrates the skin of the human body and then is inserted.

8. The surgical retractor of claim 1, wherein the fixing body further includes: a guide tube extending from a lower portion of the fixing plate to communicate with the wire hole, and configured to penetrate the skin of the body of the patient to guide the bridge member inserted through the wire hole.

9. The surgical retractor of claim 8, wherein the bridge member includes:
a locking wire locked to one of the fixing hooks of the support members;
a guide wire engaged with the locking wire to insert the locking wire into the wire hole; and
a handle engaged with the guide wire.

10. The surgical retractor of claim 9, wherein the guide wire is made of a flexible material.

11. The surgical retractor of claim 9, wherein the fixing plate has a wire fixing member for fixing the guide wire.

12. The surgical retractor of claim 11, wherein the wire fixing member includes:
a first fixing member provided on one side of an upper surface of the fixing plate, and having a primary fixing groove to which the guide wire is inserted and primarily locked; and
a second fixing member provided on the other side of the upper surface of the fixing plate, and having a secondary fixing groove formed in a perpendicular direction with respect to the first fixing groove such that the guide wire primarily locked and fixed by the first fixing member is inserted and secondarily locked.

13. The surgical retractor of claim 12, wherein a bending member is interposed between the first fixing member and the second fixing member to bend the guide wire in a curve.

14. The surgical retractor of claim 9, wherein the locking wire is formed in a shape of a closed-loop ring.

* * * * *